United States Patent [19]

Nardi et al.

[11] 4,321,120
[45] Mar. 23, 1982

[54] PROCESS FOR DETECTING PROTEINS SPECIFIC TO HYPERTENSION IN MAMMALS

[76] Inventors: Ronald V. Nardi, 6 Meadowbrook Pl., Willingboro, N.J. 08046; Prabhavathi B. Fernandes, 501 Broadacres Rd., Penn Valley, Pa. 19072

[21] Appl. No.: 131,615

[22] Filed: Mar. 19, 1980

[51] Int. Cl.³ .......................................... G01N 27/26
[52] U.S. Cl. .............................. 204/180 G; 23/230 B; 424/9; 424/101; 424/177; 260/112 B
[58] Field of Search .......... 204/180 G, 180 R, 180 S; 23/230 B, 902, 912; 424/9, 101, 177; 260/112 B

[56] References Cited

U.S. PATENT DOCUMENTS

| | | | |
|---|---|---|---|
| Re. 24,752 | 12/1959 | Ressler | 204/180 G |
| 3,129,158 | 4/1964 | Raymond et al. | 204/180 G |
| 3,384,564 | 5/1968 | Ornstein et al. | 204/180 R |
| 3,582,490 | 6/1971 | Zemel | 204/180 R |
| 3,607,695 | 9/1971 | Schnelder | 204/180 S |
| 3,687,833 | 8/1972 | Parcells et al. | 204/180 G |
| 3,719,580 | 3/1973 | Roberts et al. | 204/299 |
| 3,843,775 | 10/1974 | Wolf | 23/230 B X |
| 3,873,433 | 3/1975 | Seidel et al. | 204/180 G |
| 3,912,610 | 10/1975 | Lou | 204/180 G |
| 3,930,983 | 1/1976 | Sleber | 204/180 G |
| 3,951,776 | 4/1976 | Eibl et al. | 204/180 G |
| 3,984,532 | 10/1976 | Castro | 23/230 B X |
| 3,989,612 | 11/1976 | Kragt et al. | 204/180 G |
| 4,088,561 | 5/1978 | Anderson | 204/180 G |
| 4,094,759 | 6/1978 | Rubenstroth-Bauer et al. | 204/180 G |
| 4,123,343 | 10/1978 | Knopey et al. | 204/180 G |
| 4,124,470 | 11/1978 | Dahms | 204/180 G |
| 4,130,471 | 12/1978 | Frosch | 204/180 G |
| 4,147,606 | 4/1979 | Golian | 204/180 G |
| 4,162,208 | 7/1979 | Aladjein et al. | 204/180 G |

OTHER PUBLICATIONS

Laemmli, Nature, vol. 227 (1970) pp. 680-685.
Ames, The Journal of Biological Chemistry, vol. 249 (1974) pp. 634-644, No. 2.
Weingarten et al., Proceedings of the National Academy of Sciences, U.S.A., vol. 72, No. 5 (May, 1975) pp. 1858-1863.
Sloboda et al., Biochemistry, vol. 15 (1976) pp. 4497-4505.
Fernandes et al., Analytical Biochemistry, vol. 91 (1978), pp. 101-114.
Payne, Chromatographic and Electrophonetic Techniques, Smith, Ed., vol. II (1976) Fourth Edition.
Okamoto et al., Japanese Circulation Journal, vol. 27 (1973) pp. 282-273.
Bellini et al., Clinical Science, vol. 57 (1979) pp. 25-29.
Fernandes et al., Journal of Laboratory & Clinical Medicine, vol. 87 (1976) pp. 561-567.
Fernandes et al., Clinical Science & Molecular Medicine, vol. 54 (1978) 633-637.
West et al., "Biochemistry", 4th ed., The MacMillan Co., N.Y. p. 681.

*Primary Examiner*—Arthur C. Prescott
*Attorney, Agent, or Firm*—Seidel, Gonda, Goldhammer & Panitch

[57] ABSTRACT

A process for diagnosing the presence of hypertension or a predisposition to hypertension in a mammal comprises detecting the presence in a body fluid of the mammal of at least one protein associated with hypertension wherein the protein has a relative molecular weight of about 10,000 daltons to about 17,000 daltons. In humans, the process detects the presence of or predisposition to essential hypertension as distinguished from secondary hypertension. A preferred analytical method is discontinuous sodium dodecyl sulfate polyacrylamide gel electrophoresis.

18 Claims, 12 Drawing Figures

PROCESS FOR DETECTING PROTEINS SPECIFIC TO HYPERTENSION IN MAMMALS

BACKGROUND OF THE INVENTION

This invention relates to a new means for diagnosing the existence of or the predisposition to hypertension in a mammal, and more particularly, in a human. By use of the diagnostic process described and claimed herein, in humans it is possible to determine the existence of or predisposition to essential hypertension as opposed to secondary hypertension. The invention includes as a preferred embodiment an electrophoretic process for detecting and identifying specific proteins associated with mammalian hypertension in body fluids which were previously undetected and unidentified.

Hypertension is excessive blood pressure in the arterial system which, if left untreated, leads to disability and premature death. Hypertension is generally divided into two broad categories, essential hypertension and secondary hypertension. Essential hypertension is a familial or genetic form of elevation of blood pressure of unknown cause. Secondary hypertension is hypertension of known organic origin such as that associated with renovascular or renal parenchymal disease. The management for essential hypertension differs from that used for secondary hypertension.

By the diagnostic process disclosed and claimed herein, it will be possible to differentiate whether a patient who has hypertension is suffering from essential hypertension or from secondary hypertension. Further, by the process of the present invention, it will be possible to determine which patients may be predisposed to essential hypertension, although they presently may not have elevated blood pressure.

Hypertension is a disease of epidemic proportion affecting some 60 million people in the United States. Hypertension is a major risk factor in the eventual development of significant atherosclerotic complications, namely, myocardial infarction and stroke. Accordingly, it is very important to be able to diagnose and properly treat hypertension, whether it is essential hypertension or secondary hypertension. In addition, hypertension costs the United States more than 8 billion dollars a year in medical costs, lost productivity and lost wages. A significant amount is spent on cost-ineffective investigations directed to exclude secondary hypertension associated with a variety of causes. However it is only by exclusion of evident causes that diagnosis of essential hypertension can be made. This invention is directed to a definite and cost-effective process for the detection of a biochemical marker or markers of essential hypertension.

This invention has primary use in the clinical management of human patients. However, the treatment of other mammals, such as pets and livestock, is also considered to be within the scope of this invention.

The dividing line based on blood pressure measurements between normotension (normal blood pressure) and hypertension is not clear. While certain guidelines have been proposed, there is no absolute blood pressure above which it can be said that high blood pressure or hypertension exists. This is important in that patients or other mammals who are considered normotensive may in fact be hypertensive, and vice versa. Thus, some patients should be treated for hypertension and others should not when the same blood pressure is exhibited. The present invention will help alleviate the grey area between normotension and mild hypertension. Moreover, even when a patient undoubtedly has hypertension, there is frequently no convenient or certain method for determining whether the hypertension is the disease (essential hypertension) or whether it is caused by another disease (secondary hypertension). Since the managements differ, it is important to know which type of hypertension a patient has. The present invention allows this determination.

The present invention is primarily directed to the detection of proteins associated with hypertension in humans and in mammals generally. The preferred process is the use of high resolution discontinuous sodium dodecyl sulfate (sodium dodecyl sulfate will be abbreviated "SDS" hereinafter) polyacrylamide gel electrophoresis, although other qualitative and quantitative methods for the detection of proteins in body fluids may be used.

SDS polyacrylamide gel electrophoresis is a technique that has been used in analyzing protein components of eukaryotic and prokaryotic preparations. For example, see Laemmli, U. K., Nature 277: 680–685, 1970; Ames, G. F. L., Journal of Biological Chemistry 249: 634–644, 1974; Weingarten, M. D., Lockwood, A. H., Hwo, S. Y. & Kirshner, M. W., Proceedings of the National Academy of Sciences, U.S.A. 72: 1858–1863, 1975; Sloboda, R. D., Dentler, W. C. & Rosenbaum, J. L., Biochemistry 15: 4497–4505, 1976; and Fernandes, P. B., Nardi, R. V. & Franklin, S. G., Analytical Biochemistry 91: 101–114, 1978.

Despite these investigations, it is believed that prior to the present invention no one has considered using an electrophoretic gel process for determining the differences between normotensive and hypertensive mammals or the differences between mammals having essential hypertension and mammals having secondary hypertension. It is believed that this is partly because it is generally accepted that essential hypertension represents high blood pressure without evident cause, so that a specific search for biochemical "markers of disease", such as the proteins detected and identified herein, did not appear relevant. Furthermore, until the inventors discovered the existence of proteins associated with at least a predisposition to hypertension, no one could have conceived of a method of detecting and/or identifying them.

Electrophoretic gel analysis has been used to detect other diseases or pathological problems (see, for example, U.S. Pat. No. 3,607,695 of Schneider, issued Sept. 21, 1971 and U.S. Pat. No. 3,687,833 of Parcells et al, issued Aug. 29, 1972), but the use of gel electrophoresis has not been considered with respect to the determination of factors affecting hypertension.

SUMMARY OF THE INVENTION

The present invention is based upon the discovery that a particular protein (or proteins) in body fluids is associated with hypertension in mammals, including human patients. The inventors have discovered that the protein or proteins are biochemical markers for patients with or predisposed to essential hypertension, as compared to secondary hypertension.

The present invention comprises a process for diagnosing the presence of hypertension or a predisposition to hypertension in a mammal comprising detecting the presence in a body fluid of the mammal of at least one protein associated with hypertension, the protein having a relative molecular weight of about 10,000 daltons to about 17,000 daltons.

In a preferred embodiment, the protein is detected by discontinuous SDS polyacrylamide gel electrophoresis. A further preferred technique is to use a gradient of concentrations of polyacrylamide gel as the resolving gel in the electrophoretic technique. Additionally, another preferred method of detecting the protein or proteins associated with hypertension is to use a horizontal polyacrylamide gel concentration gradient technique wherein there is in the horizontal gradient gel a protein band representative of the protein associated with hypertension which displays migration of the protein associated with hypertension from a first position corresponding to a first relative molecular weight to a second position corresponding to a second relative molecular weight greater than the first relative molecular weight. This may be displayed on the horizontal gradient gel by a protein band which crosses over or approaches an adjacent protein band. This is a very unusual occurrence and is characteristic of the protein associated with hypertension in the relative molecular weight range of about 10,000 daltons to about 17,000 daltons.

BRIEF DESCRIPTION OF THE DRAWINGS

Photographs and ink drawings are provided for the purpose of illustrating a preferred analytical technique according to the present invention. It should be understood, however, that this invention is not limited to the precise techniques, determinations and results illustrated in the photographs and drawings.

DESCRIPTION OF THE PREFERRED EMBODIMENTS

Figure 1:
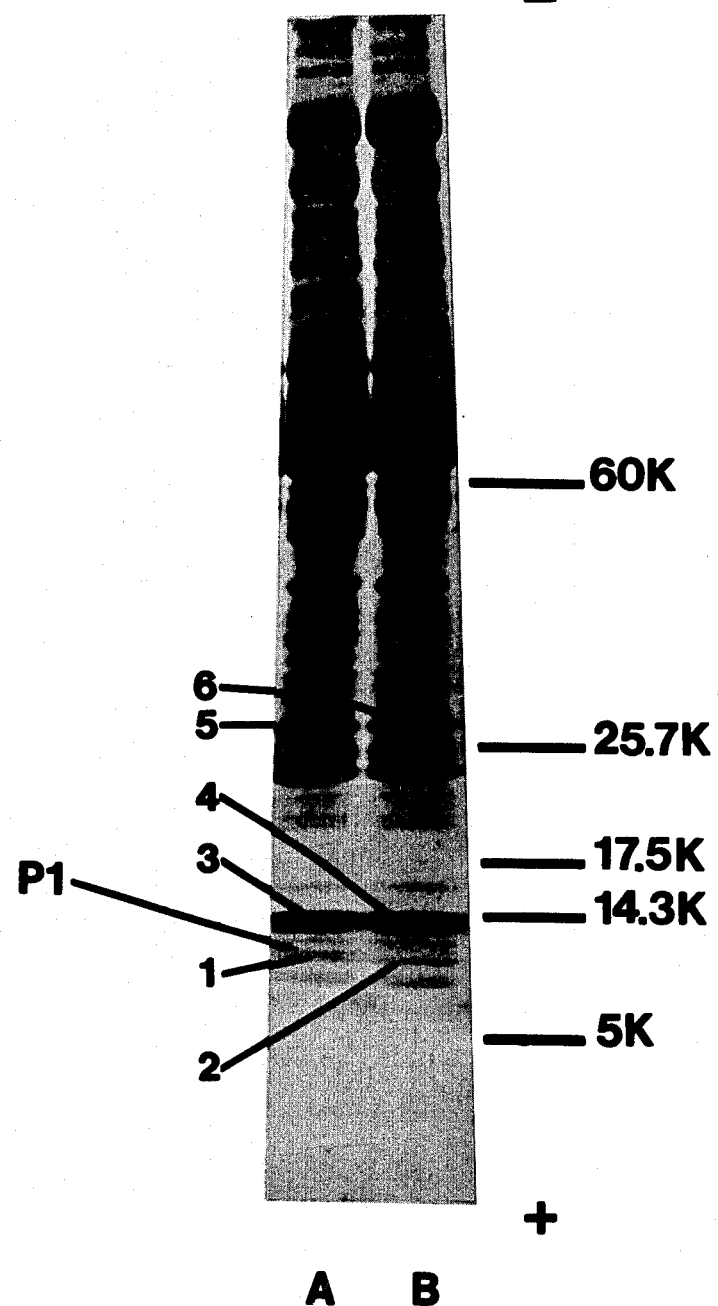
FIG. 1 is a photograph of a SDS polyacrylamide gel comparing protein bands representative of proteins present in blood plasma from a spontaneously hypertensive rat with protein bands representative of proteins present in blood plasma from a normotensive control rat.

The present invention will be described with respect to a particular process for diagnosing the presence of hypertension or a predisposition to hypertension in a mammal comprising detecting the presence in a body fluid of the mammal of at least one protein associated with hypertension, the protein having a relative molecular weight of about 10,000 daltons to about 17,000 daltons.

The particular process described in detail herein is the process of discontinuous SDS polyacrylamide gel electrophoresis. However, it should be understood that the process for diagnosing the presence of the particular protein or proteins associated with hypertension need not be limited to SDS polyacrylamide gel electrophoresis, electrophoresis techniques in general, or any other particular process or technique for determining the existence of the protein or proteins associated with hypertension. Thus, once the discovery upon which this invention is based becomes known, any suitable technique for detecting the presence of the protein or proteins associated with hypertension will be satisfactory. As explained hereinbefore, the discovery upon which this invention is based is that there is at least one particular protein in a mammal's body fluid which is associated with hypertension, and with respect to humans, the protein is associated only with essential hypertension. Thus, the protein, once identified, will be a "marker" for the disease. Anyone who is capable of detecting and identifying the marker protein by any analytical technique, be it qualitative or quantitative, will be using this invention.

SDS polyacrylamide gel electrophoresis has been chosen as a preferred diagnostic process for detecting the presence of the protein or proteins associated with hypertension because it is a readily available technique. The equipment and reagents used in SDS polyacrylamide gel electrophoresis are readily available commercially and presently form part of the standard equipment of many clinical laboratories. Additionally, a large number of samples of body fluids can be run simultaneously, efficiently and economically using standard SDS polyacrylamide gel electrophoresis equipment.

Other suitable methods of detecting and identifying the presence of a protein or proteins associated with hypertension may be the well-known analytical techniques including, for example and not by way of limitation, various chromatographic techniques, such as high pressure liquid chromatography, thin layer chromatography, starch gel chromatography, silica gel chromatography; other types of electrophoresis, such as starch gel electrophoresis, silica gel electrophoresis; antibody-antigen interactions and related immunological technology such as immune precipitation, immune electrophoresis, enzyme-linked immunosorbent assay and radioimmunoassay, and the like. Several of the electrophoretic and chromatographic techniques which are suitable for use in detecting the protein or proteins associated with hypertension are described in Smith, I., Ed., Chromatographic and Electrophoretic Techniques, Volume II, Zone Electrophoresis, 4th Edition, Year Book Medical Publishers, Inc., Chicago, 1976; Chapter 12, Payne, J. W., "Electrophoresis of Proteins on Sodium Dodecyl Sulphate Polyacrylamide Gels" generally describes the preferred process used with the present invention.

The preferred process of detecting proteins associated with hypertension is an electrophoretic determination. A small sample of the body fluid to be tested is applied to a solid electrophoretic support medium, preferably SDS polyacrylamide gel. It will be understood, however, that other support media may be used, such as for example cellulose acetate, cellulose nitrate, agar, agarose, paper, cellulose, silica gel, starch gel, and the like.

The apparatus used for discontinuous SDS polyacrylamide gel electrophoresis is widely available commercially, such as from Aquebogue Machine & Repair Shop, Aquebogue, N.Y. It generally comprises two glass plates separated from each other by spacer strips of inert material, such as methyl methylacrylate. The spacer strips are used between the plates along each side edge and the bottom edge. The assembly is clamped together and the edges are sealed such as by dripping agar or the like around the outside edges.

A resolving gel is poured between the plates until the space between the plates is approximately 75% to 90% full. After the gel has set, an inert spacer in the shape of a comb is inserted between the plates at the upper portion thereof to form sample wells to receive samples of the body fluid to be tested. A spacer gel is poured between the plates around the comb and allowed to set. The comb and the bottom spacer strip are then removed.

The sample receiving apparatus is then clamped in an electrophoresis apparatus so that an upper chamber of electrode buffer is in contact with the gel at the upper portion of the sample receiving apparatus and a lower electrode buffer is in contact with the gel at the lower portion of the sample receiving apparatus. A cathode is immersed in or connected to the upper buffer container and an anode is immersed in or connected to the lower buffer container. Either constant current or constant voltage may be applied to the anode and cathode to cause the migration of proteins in the body fluid sample through the gel. The use of constant current is presently preferred. The amount of the current or voltage is well known to those of ordinary skill in the art. Typical currents are 30 milliamperes which is used for a run lasting about 4 to 4.5 hours. 8 milliamperes can be used for a run lasting about 16 to about 17 hours. Typical voltages are 30–300 volts. The current or voltage is maintained until the deired degree of migration of the proteins in the sample is achieved.

The general technique for preparing the resolving gel, spacer gel, electrode buffer and sample buffer are well known to those of ordinary skill in the art, having been described in Laemmli, U. K., Nature 227: 680–685, 1970; and Fernandes P. B., Nardi, R. V. and Franklin, S. G., Analytical Biochemistry 91: 101–114, 1978.

An example of a suitable resolving gel includes the following ingredients. An acrylamide-bis-acrylamide stock solution is prepared using 60 g acrylamide and 1.6 g N,N'-methylene-bis-acrylamide per 100 ml of solution, the balance being water. Other formulations are possible. For example, other cross-linking agents may be used instead of N,N'-methylene-bis-acrylamide, such as, for example, dihydroxyethylene-bis-acrylamide or bis-acrylylcystamine. As the cross-linking agent and the ratio of cross-linker to the monomer is changed, different characteristics result which can be tailored as desired by one of ordinary skill in the art. The ratio of monomer to cross-linking agent, such as acrylamide to N,N'-methylene-bis-acrylamide determines the sieving property of the gel and thereby the optimum resolution conditions.

The polymerization of the acrylamide and N,N'-methylene-bis-acrylamide solution is catalyzed by N, N, N', N'-tetramethylene diamine (hereinafter "TEMED") and ammonium persulfate (hereinafter "APS"). Riboflavin and light may also be used to catalyze polymerization of the acrylamide gel. The resulting gel also contains Tris-HCl buffer with pH 8.8, SDS, and glycerol, if desired for purposes discussed hereinafter.

As used herein, the term "%" or "percent" means the weight to volume percent of the particular ingredient in the composition or component being described, unless otherwise indicated in the context of the description. Thus, for example, the following description is directed to the percentage of the ingredients in the resolving gel and the percentage of each is the final percentage of the ingredient in the resolving gel.

The Tris-HCl may be adjusted to yield a final concentration of about 0.15 M to about 0.75 M in the gel. The presently preferred concentration is 0.375 M. The SDS concentration may be adjusted to a final concentration in the gel of up to about 0.5%, 0.1% being presently preferred. The acrylamide portion of the gel (and hence, the polyacrylamide gel) may be adjusted to have a uniform acrylamide concentration or a gradient of acrylamide concentration. When a uniform acrylamide concentration is used, it should be present in about 10% to about 20% to detect the specific variation in protein composition in samples of body fluids from mammals. The presently preferred uniform concentration of acrylamide is about 13% to about 14%. Uniform concentrations of acrylamide above 20% are possible, but do not appear to be more advantageous.

Gradients of acrylamide concentration may be used in the resolving gel with various end concentrations between about 5% and about 30% to detect specific variation in protein compositions in samples of body fluids from mammals being tested. Gradients of acrylamide concentration may be adjusted exponentially or linearly for example. Examples of satisfactory gradient concentrations of acrylamide include exponential gradients of about 8% to about 25%, about 12% to about 20%, and about 12% to about 30%; and linear gradients of about 10% to about 25%. Glycerol is not necessary but may be added to the acrylamide to stabilize the gradient concentrations when gradient concentrations are being used. The glycerol may be used in amounts of up to about 10%.

The spacer gel includes Tris-HCl buffer with pH 6.8, SDS, and acrylamide prepared from the stock solution of acrylamide and bis-acrylamide. The polymerization of the acrylamide solution is catalyzed with TEMED and APS. The acrylamide concentration may vary between about 3% and about 6%, 6% being the presently preferred concentration, since above 6% higher molecular weight proteins are sieved. The concentration of the Tris-HCl buffer may be adjusted to be about 0.060 M to about 0.250 M, 0.125 M being presently preferred. The SDS concentration is the same as in the resolving gel.

An electrode buffer solution is poured into the upper and lower buffer chambers of the electrophoresis apparatus. The electrode buffer solution is prepared by adding 3.0 g of Tris, 14.4 g. glycine, SDS to a final concentration in the electrode buffer solution of 0.1%, and a sufficient amount of water to bring the total volume of the electrode buffer solution to 1 liter. The electrode buffer solution has an approximate pH 8.3. The concentrations of Tris and glycine may be doubled to change the time it takes for the proteins to migrate.

Body fluids to be tested for the presence of at least one protein associated with hypertension may include urine, blood plasma, blood serum or any other protein-containing body fluid. A sample of a body fluid to be tested, diluted if desired with deionized water, is mixed with an equal volume of sample buffer to give a sample solution. One composition for a suitable sample buffer includes about 0.050 M to about 0.125 M Tris-HCl pH 6.8, a preferred amount being 0.050 M; about 5.0% to about 20% of glycerol, a preferred amount being 10%; about 1.0% to about 8% of SDS, a preferred amount being 4%. Prior to boiling the sample solution, a tracking dye, such as bromophenol blue, is used in the sample buffer. Other suitable dyes may be used instead of bromophenol blue. A reducing agent, such as 2-mercaptoethanol (having a final concentration in the total sample solution of about 5% to about 10%) is added. Other reducing agents such as dithiothreitol, dithioerythritol, etc., may be used to reduce the disulfide bonds in the amino acid groups in the proteins.

The sample solution is boiled for about 2 to about 5 minutes in a capped tube. After cooling, an aliquot of each of the various sample solutions are placed in each of the sample wells in the spacer gel, the current is applied and electrophoresis is performed. When the tracking dye and the proteins have migrated an appropriate distance, the current is shut off and visualization of the protein bands as illustrated in FIG. 1, for example, is produced by standard Coomassie Brilliant Blue R 250 staining procedures. The gels may then be analyzed and dried. The gels may be photographed for recordation and/or analysis.

The invention will now be described in more detail with reference to the following specific, non-limiting examples relating to the procedure, results and analysis of exemplary body fluids, namely urine and blood plasma, from laboratory rats and human patients.

Example 1

Figure 2:
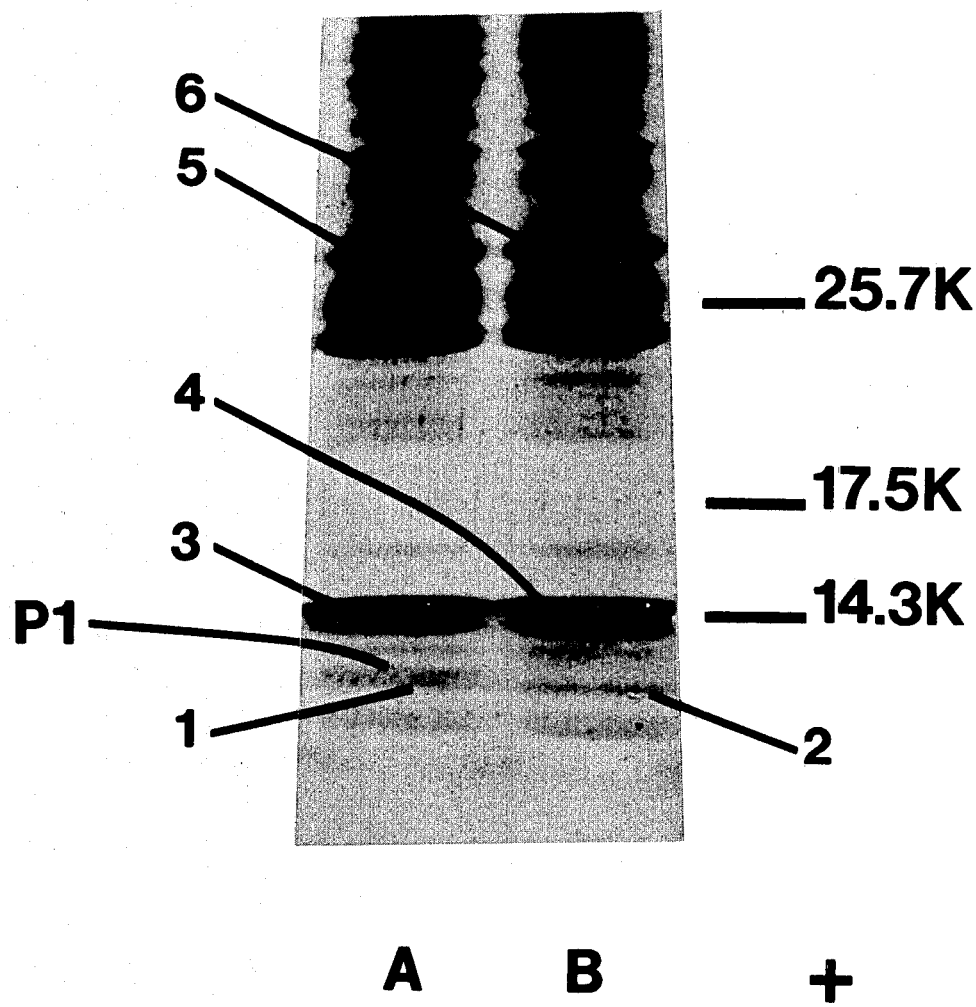
FIG. 2 is an enlargement of the lower portion of FIG. 1 which is of primary interest.
Figure 3:
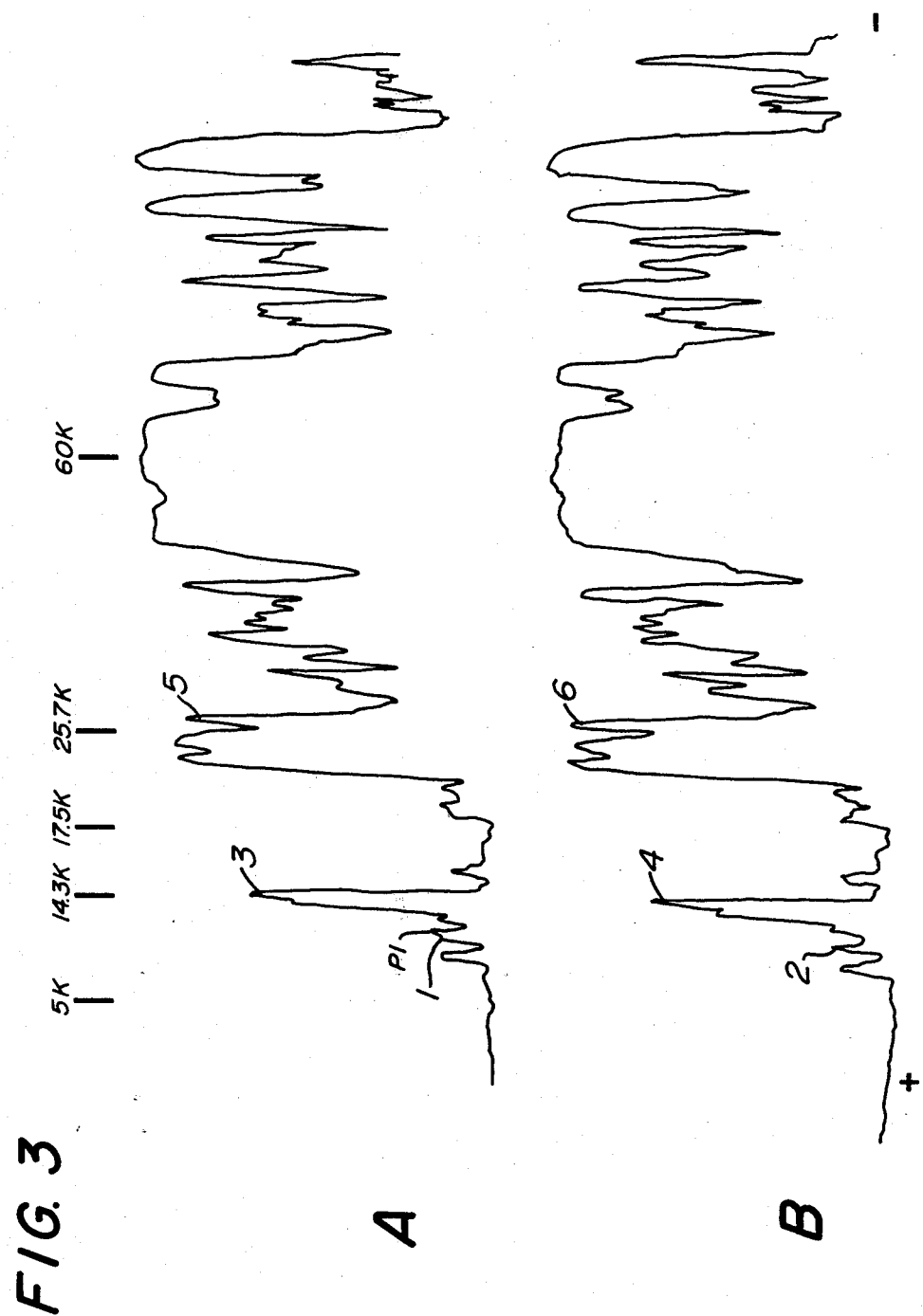
FIG. 3 is a scan of the photograph of FIG. 1 using a soft laser scanning densitometer in a high resolution mode.

This example is representative of experiments done with two groups of laboratory rats to compare the proteins in the blood plasma of genetically bred hypertensive rats with the proteins present in the blood plasma of normotensive control rats. The results of a discontinuous SDS polyacrylamide gel electrophoretic analysis are illustrated in FIGS. 1 through 3.

The genetically bred hypertensive rats used in the experiments of which this example is representative were spontaneously hypertensive rats (hereinafter "SHR") bred as set forth in Okamoto, K. and Aoki, K., Japanese Circulation Journal 27: 282–293, 1963, and were obtained from the National Institutes of Health, Bethesda, Maryland, U.S.A. The normotensive control rats were the genetic parents of the SHR, namely Wistar Kyoto rats, obtained from the same source as the SHR rats. The Wistar Kyoto normotensive control rats will be referred to hereinafter as "WKYN".

Both groups of rats were maintained on Purina Lab Chow and water ad libitum. Direct arterial pressure was measured through an indwelling Teflon-Tygon catheter placed in the left common carotid artery of the rats. Concerning the two rats whose gels were selected for this Example, the blood pressure of the SHR rat was 212/134 mm Hg systolic/diastolic and the blood pressure of the WKYN rat was 134/100 mm Hg. Based on the great difference between these values, it is readily apparent that the SHR rat was hypertensive. The hypertension was caused by genetic factors. Accordingly, the SHR rat is considered to be a model of human hypertension and, more particularly, a model of human essential hypertension.

Blood was obtained from conscious rats through the carotid artery catheter and placed into cold heparinized tubes. Plasma and cellular components were separated by centrifugation and the plasma was stored at $-80°$ C. The plasma proteins were resolved by discontinuous SDS polyacrylamide gel electrophoresis using the apparatus and compositions described hereinbefore and set forth more particularly as follows.

The resolving gel comprised acrylamide in an exponential gragradient from 8 to 25% prepared by standard techniques using a 10 ml mixing volume. Tris-HCl, pH 8.8, was present in a concentration of 0.375 M. SDS concentration was 0.1% and glycerol was present in exponential gradient concentrations from 0 to 10%.

The spacer gel included 6% acrylamide, 0.125 M Tris-HCl at pH 6.8, and 0.1% SDS.

The sample buffer had the following ingredients whose percentages are expressed as the final concentration diluted with an equal volume of the sample: 0.025 Tris-HCl at pH 6.8, 5% glycerol, and 2% SDS.

The electrode buffer contained 3.0 g Tris, 14.4 g glycine, 0.1% SDS and water to make 1 liter. The electrode buffer had a final pH 8.3.

The blood plasma sample solutions were prepared by diluting the plasma 1:10 with deionized water and then mixing the diluted samples one to one with the sample buffer. 2-mercaptoethanol to a final concentration of 5% was added to the sample solution and this solution was boiled for 2–5 minutes in a capped tube. An aliquot of about 40 μl of sample solution from each rat was electrophoresed in a vertical orientation at a constant current of about 10 mA overnight. The results of the two electrophoresed samples are illustrated in FIG. 1, which is a photograph of the actual gels obtained. FIG. 2 is an enlargement of the left-hand portion of FIG. 1 showing the area of primary interest, and FIG. 3 is a scan of a transparency of the photograph of FIG. 1 using a soft laser scanning densitometer (Biomed Instruments, Inc.) in the high resolution mode.

With reference to FIGS. 1 and 2 wherein like letters and numerals represent like elements, gel A is the gel of the plasma sample from the SHR rat. Gel B is the gel of the sample from the WKYN rat. Various marker proteins having known molecular weights were electrophoresed simultaneously adjacent to the samples so that relative molecular weight of the proteins in the samples could be determined by interpolation. The marker proteins included insulin, represented by "5K" (5K indicates a molecular weight of about 5,000 daltons); lysozyme at 14.3K; tobacco mosaic virus coat protein at 17.5K; chymotrypsinogen at 27.5K; and catalase at 60K. These marker proteins were used as standards throughout all examples contained herein except for Examples 2 and 3.

In addition to the marker proteins identified by their relative molecular weights on the right-hand side of the photographs, several additional indicator proteins present in the sample solution were used to help determine the relative molecular weight of the protein or proteins associated with hypertension in the samples. The indicator proteins, generally indicated in the Figures by numerals, are generally represented on the gels and the photographs of the gels by relatively dark bands for which relative molecular weights may be easily interpolated.

Reviewing gel A and gel B in FIGS. 1 and 2, it is apparent that they are substantially identical except for one horizontal band P1 which is present in gel A but not in gel B. Protein band P1 has been found to be representative of the protein associated with hypertension. Thus, the only apparent difference between gel A and gel B is the existence of protein band P1, and the only apparent difference between the two rats is that rat A has genetically derived hypertension while rat B is normotensive. Protein bands 1 and 2 represent the first same indicator protein used to determine the relative molecular weight of P1. Proteins bands 3 and 4 represent the same second indicator protein. Protein bands 5 and 6 represent the same third indicator protein. The indicator protein represented by bands 1 and 2 has a molecular weight of about 12,400 daltons. The protein represented by bands 3 and 4 has a molecular weight of 15,300 daltons. The indicator protein represented by bands 5 and 6 has a molecular weight of about 27,500 daltons. Using the molecular weight of the indicator proteins and the marker proteins, the calculated relative molecular weight (hereinafter "MWr") of P1 is about 12,800.

The word "about" when used herein with respect to molecular weights, means ±10%. Thus, when "about" is used, it is used because the analytical technique in combination with the calculation for determining the molecular weights of the proteins gives a result that is precise within a range of approximately 10%.

As used herein, the term "relative molecular weight" or "MWr" means the molecular weight of a protein based upon the relative position of its representative protein band with respect to the protein bands representative of the indicator proteins and the marker proteins. Because the molecular weight is not absolute, the unit "daltons" is not used with respect to "relative molecular weight" or "MWr".

It has been determined that protein band P1 does not represent any of the proteins usually considered to be related to hypertension, namely renin, renin-substrate or angiotensin. This conclusion was reached on the basis of molecular weight determinations. Thus, while the protein associated with hypertension represented by band P1 has a MWr of about 12,700, the molecular weight of renin is about 37,000 to about 43,000 daltons. The molecular weight of renin-substrate is species dependent and ranges from about 56,000 to 110,000 daltons. The molecular weight of angiotensin 1 and 11 are 1457 and 1171 daltons, respectively. Accordingly, P1 appears to be a band representative of a previously unknown protein associated with hypertension.

FIG. 3 is a scan of a transparency of the gel of FIG. 1 using a soft laser scanning densitometer. With this instrument, the density of the protein bands in the transparency can be measured. The scan is labeled to correspond with the labeling of FIG. 1 and FIG. 2. Thus, peak 1 and peak 2 of FIG. 3 represent the same protein represented by bands 1 and 2 in FIG. 1. Likewise with bands 3, 4 and 5, 6. Clearly, there is a difference in scan A and scan B in FIG. 3. Peak P1 of scan A is not completely separate from peak 1 of scan A because the protein represented by peak P1 is not well resolved from the protein represented by peak 1. Nevertheless, it is clear that there is a qualitative difference between the respective areas of scan A and scan B in the vicinity of peak P1. The scan of FIG. 3 highlights the existence of the protein associated with hypertension as represented by protein band P1 in gel A for the SHR rat in FIGS. 1 and 2.

EXAMPLE 2

This example is representative of a series of experiments comparing the proteins in urine samples from the SHR genetically hypertensive rat and the normotensive WKYN rat. Photographs of electrophoretic gels reveal the existence of a protein associated with hypertension present in the gel of the urine sample of the SHR rat which is not present in the otherwise substantially identical gel of the WKYN rat.

The SHR rats and the genetically parental age-matched WKYN rats were obtained from the National Institutes of Health, and were maintained on Purina Lab Chow and water ad libitum. Urine was collected overnight and stored at $-80°$ C. An indwelling Teflon-Tygon catheter was placed in the left common carotid artery of each rat. Direct arterial blood pressure was measured through the catheter in conscious rats. The SHR rat had a blood pressure of 210/164 mm Hg and the WKYN rat had a blood pressure of 124/100 mm Hg. Thus, it is clear that the SHR rat was hypertensive and the WKYN rat was normotensive.

Proteins from unconcentrated urine samples were resolved by discontinuous SDS polyacrylamide gel electrophoresis. Gels with vertical exponential concentration gradients of acrylamide (from 12 to 25% using a 10 ml mixing volume) were prepared. The composition of the resolving gel, spacer gel, electrode buffer and sample buffer were the same as those set forth in Example 1 as were the electrophoresis conditions except as described below. An aliquot of about 40 $\mu$g of urine protein from the urine sample solution from each rat was prepared by mixing equal volumes of urine and sample buffer (50 $\mu$l of sample solution frm the WKYN rat and 75 $\mu$l of sample solution from the SHR rat). The samples were electrophoresed simultaneously adjacent to a solution containing the marker proteins identified on the right-hand side of FIGS. 4 and 5 by their molecular weights: lysozyme (14.3K), soybean trypsin inhibitor (21K), carbonic anhydrase (29K), ovalbumin (43K), and albumin (68K). The results of this electrophoresis are illustrated in FIGS. 4 and 5.

Figure 4:
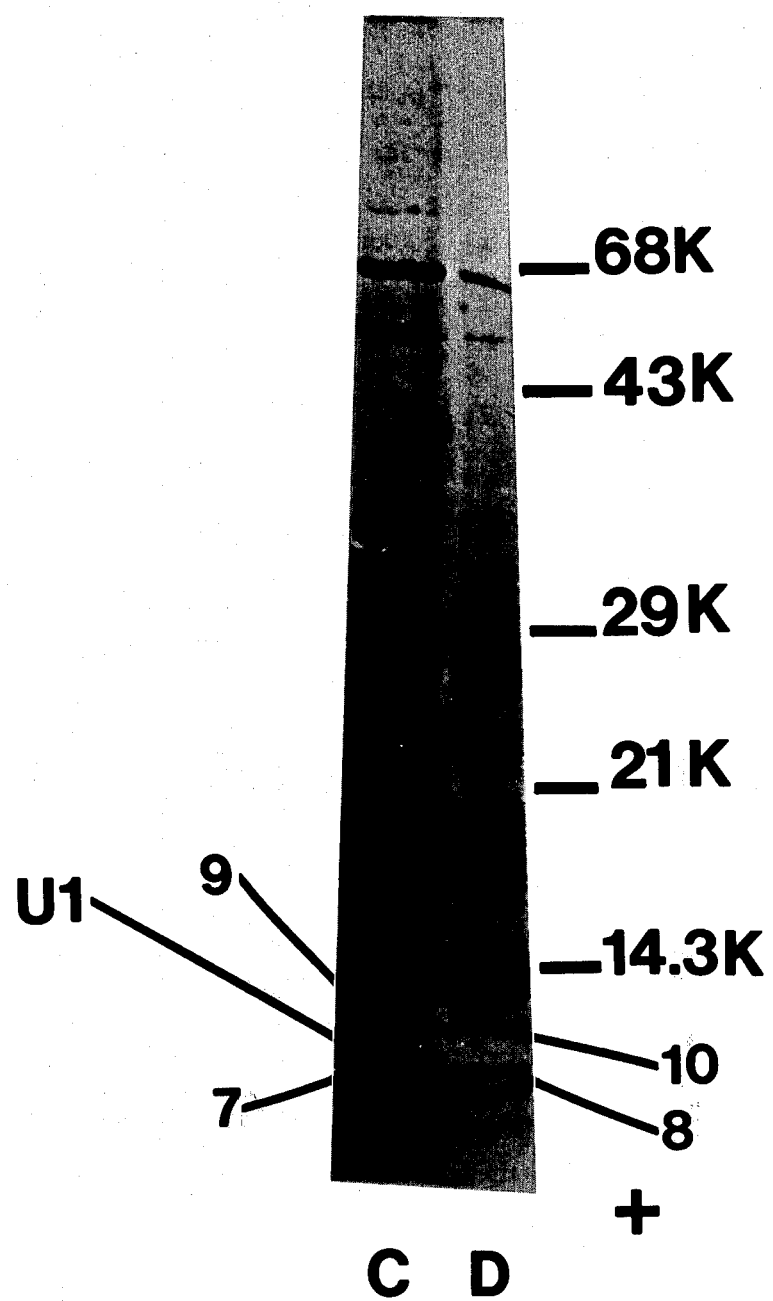
FIG. 4 is a photograph of a SDS polyacrylamide gel comparing protein bands representative of proteins in urine from a spontaneously hypertensive rat with protein bands representative of proteins present in urine from a normotensive control rat.
Figure 5:
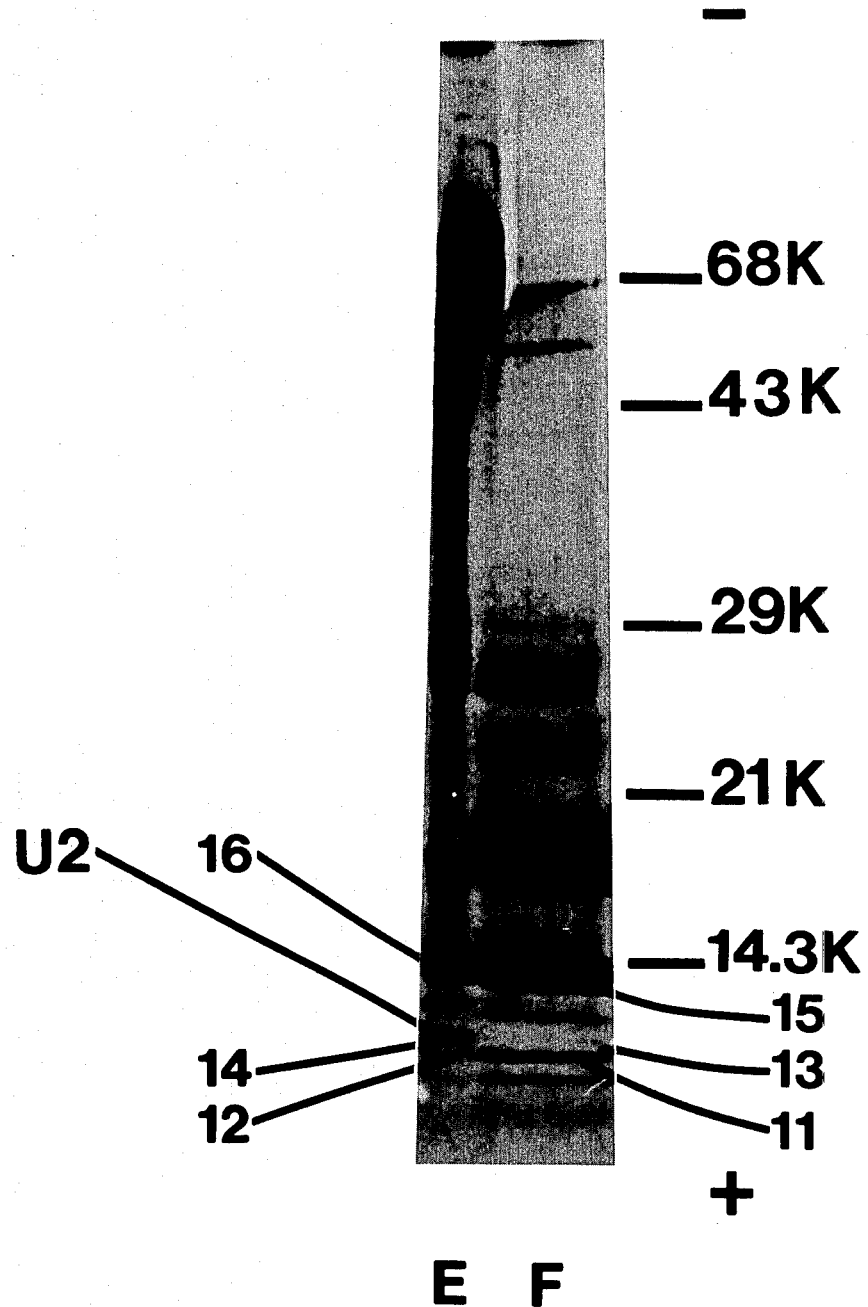
FIG. 5 is photograph of a SDS polyacrylamide gel comparing protein bands representative of proteins in urine from a rat made hypertensive by a surgical technique to serve as a model of secondary renal hypertension with protein bands representative of proteins present in urine from a normotensive control rat subjected to a sham surgical operation.

FIG. 4 is a photograph of the gels of the urine sample from the SHR rat (gel C) and from the WKYN rat (gel D). Upon inspecting gels C and D, it is clear that gel C contains an additional protein band, identified as U1 (between indicator protein bands 7 and 9) when compared with gel D. Otherwise, gels C and D are substantially identical. Protein bands 7 and 8 in FIG. 4 represent the same first indicator protein having a molecular weight of 10,600 daltons. Protein bands 9 and 10 represent the same second indicator protein having a molecular weight of 12,200 daltons. Protein band U1 represents the protein associated with hypertension in the SHR rat having a relative molecular weight of about 11,400 interpolated from the molecular weights of the indicator proteins and marker proteins.

Based on the MWr of the protein represented by band U1, this protein is not renin, renin-substrate or angiotensin. Accordingly, it is believed that protein band U1 is representative of a previously undiscovered protein associated with hypertension.

Since the rats are substantially identical, except that the SHR rat has genetically derived hypertension, and since the proteins in the urine samples are substantially identical, except for the presence of protein band U1 in gel C, it has been determined that band U1 represents a protein associated with hypertension. No laser scanning densitometer scan was made of a transparency of FIG. 4 because it is believed that the existence of protein band U1 is sufficiently clear in FIG. 4.

EXAMPLE 3

This example is representative of experiments to determine what protein distinctions exist in body fluids, particularly urine in this specific example, from laboratory rats which have been surgically treated to serve as models of renal hypertension, one form of secondary hypertension.

Male Sprague-Dawley rats were used for this experiment. They were maintained on standard Purina Lab Chow and water ad libitum. Arterial pressure was measured through an indwelling Teflon-Tygon catheter inserted in the left common carotid artery. One group of rats was surgically treated by the total ligation of the aorta between the renal arteries and just below the origin of the superior mesenteric artery to produce an experimental model of severe renal hypertension. These rats which were surgically treated to be experimental models of renal hypertension will be referred to hereinafter as "ERH" rats. The surgical method is believed to be known to those or ordinary skill in the art and if further details concerning the procedure are desired, attention is directed to Fernandes, M., Onesti, G., Weder, A., Dykyj, R., Gould, A. B., Kim, K. E. & Swartz, C., Journal of Laboratory and Clinical Medicine, 87: 561-567, 1976; Fernandes, M., Fiorentini, R., Onesti, G., Bellini, G., Gould, A. B., Hessan, H., Kim, K. E. & Swartz, C., Clinical Science & Molecular Medicine, 54: 633-637, 1978; and Bellini, G., Fiorentini, R., Fernandes, M., Onesti, G., Hessan, H., Gould, A. B., Bianchi, M., Kim, K. E. & Swartz, C., Clinical Science, 57: 25-29, 1979.

A group of age-matched male Sprague-Dawley rats were used as controls. To have a fair comparison, the control rats were subjected to a sham operation in which they were incised, and the aorta between the renal arteries below the superior mesenteric artery was manipulated, but not ligated. After 40 days, aliquots of urine samples were taken from both groups of rats and subjected to discontinuous SDS polyacrylamide gel electrophoresis using the same gel and buffer compositions and conditions as in Example 2. The sizes of the samples were adjusted to provide easily visible protein bands in the region of interest, namely about 10,000 daltons to about 17,000 daltons. 20 $\mu$l of sample solution from the EHR rat and 50 $\mu$l of sample solution from the normotensive rat were used. The same marker proteins were used as were used in Example 2.

Two of the gels that were photographed comprise FIG. 5.

Gel E shows the resolution of the urine proteins in the ERH rat 40 days after the operation to make it a renal hypertensive model. The ERH rat had a blood pressure of 228/152 mm Hg. Gel E shows the resolution of the urine proteins in the control rat 40 days after the sham operation. The control rat had a blood pressure of 128/104 mm Hg.

The urine from the ERH rat (gel E) contained large amounts of protein including high molecular weight species, such as albumin, having a molecular weight of about 68,000 daltons. The urine of the normotensive control rat contained only small amounts of protein species with molecular weights above 25,000 daltons. This may indicate some defect in the filtration process in the ERH rats. However, the protein composition of the urine of the normotensive control and ERH rats is similar for protein species below 25,000 daltons except as indicated below.

The urine from the ERH rat (gel E) contains only one additional protein band labeled U2 when compared with the gel from the normotensive control rat (gel F) in the range below 25,000 daltons.

The calculated MWr of the protein represented by band U2 is 11,400 based on the molecular weights of the marker proteins and indicator proteins. Protein bands 11 and 12 represent the same first indicator protein having a molecular weight of 10,600 daltons. Protein bands 13 and 14 represent the same second indicator protein having a molecular weight of 11,200 daltons. Protein bands 15 and 16 represent the same third indicator protein having a molecular weight of 14,300 daltons.

Because FIG. 5 clearly indicates the existence and relative location of protein band U2, there is no corresponding scan of a transparency of FIG. 5 using a laser scanning densitometer.

Based on the MWr of U2, this protein associated with hypertension is not renin, renin-substrate or angiotensin. Accordingly, the logical conclusion is that protein band U2 is representative of a protein associated with hypertension.

EXAMPLE 4

This example is representative of experiments directed to the detection and identification of proteins associated with hypertension in blood plasma of laboratory rats surgically treated to be models of renal hypertension. The surgical technique was the same as the technique described with respect to Example 3. One additional modification was used in this example as described hereinafter.

Figure 6:
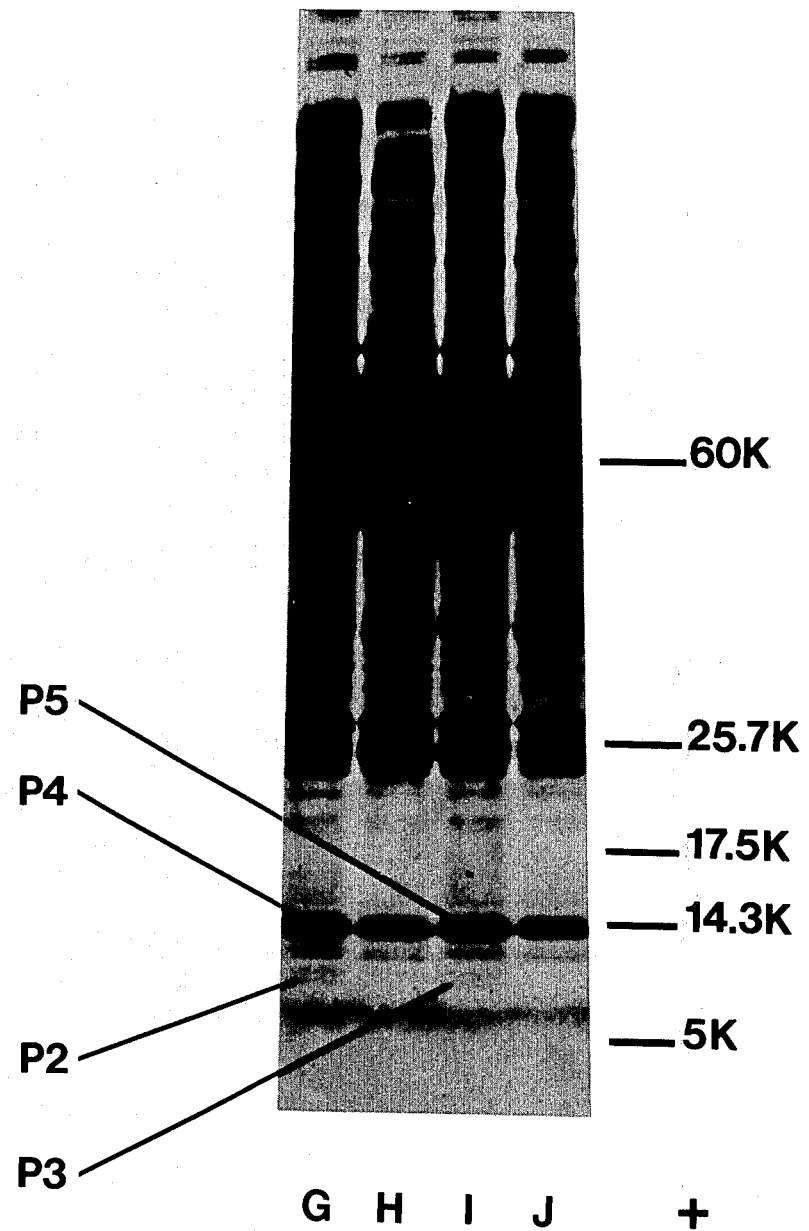
FIG. 6 is a photograph of a SDS polyacrylamide gel comparing protein bands representative of proteins in blood plasma of rats made hypertensive by a surgical technique to serve as models of secondary renal hypertension with protein bands representative of proteins in blood plasma from a normotensive control rat, and from a hypertensive rat rendered normotensive by removal of the ischemic kidney.
Figure 7:
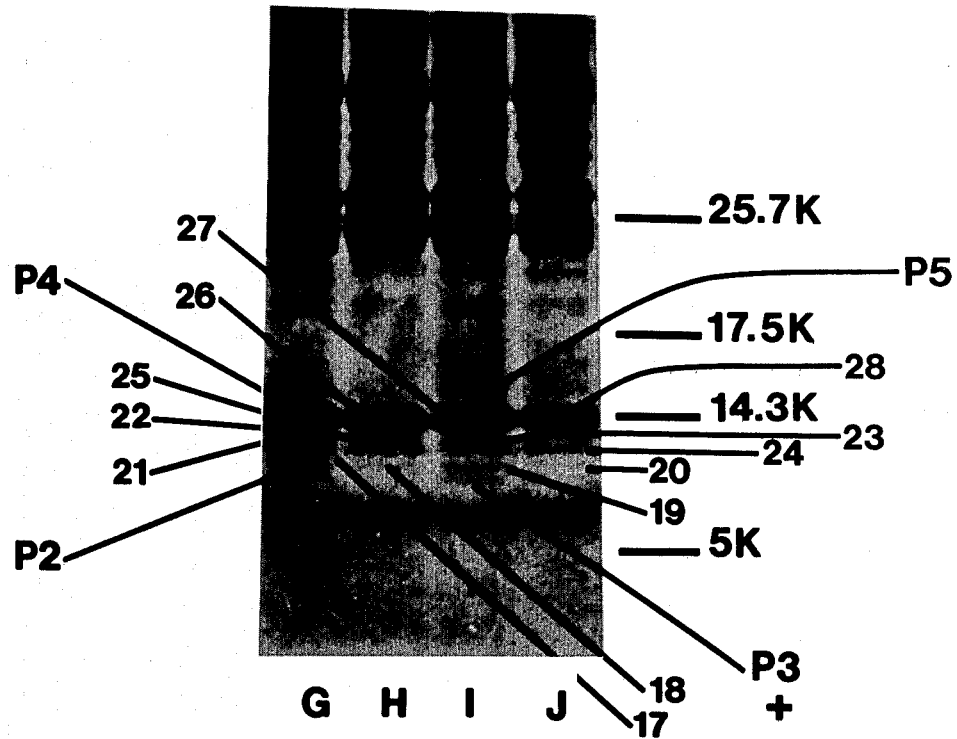
FIG. 7 is an enlargement of the lower portion of FIG. 6 which is of primary interest.
Figure 8:
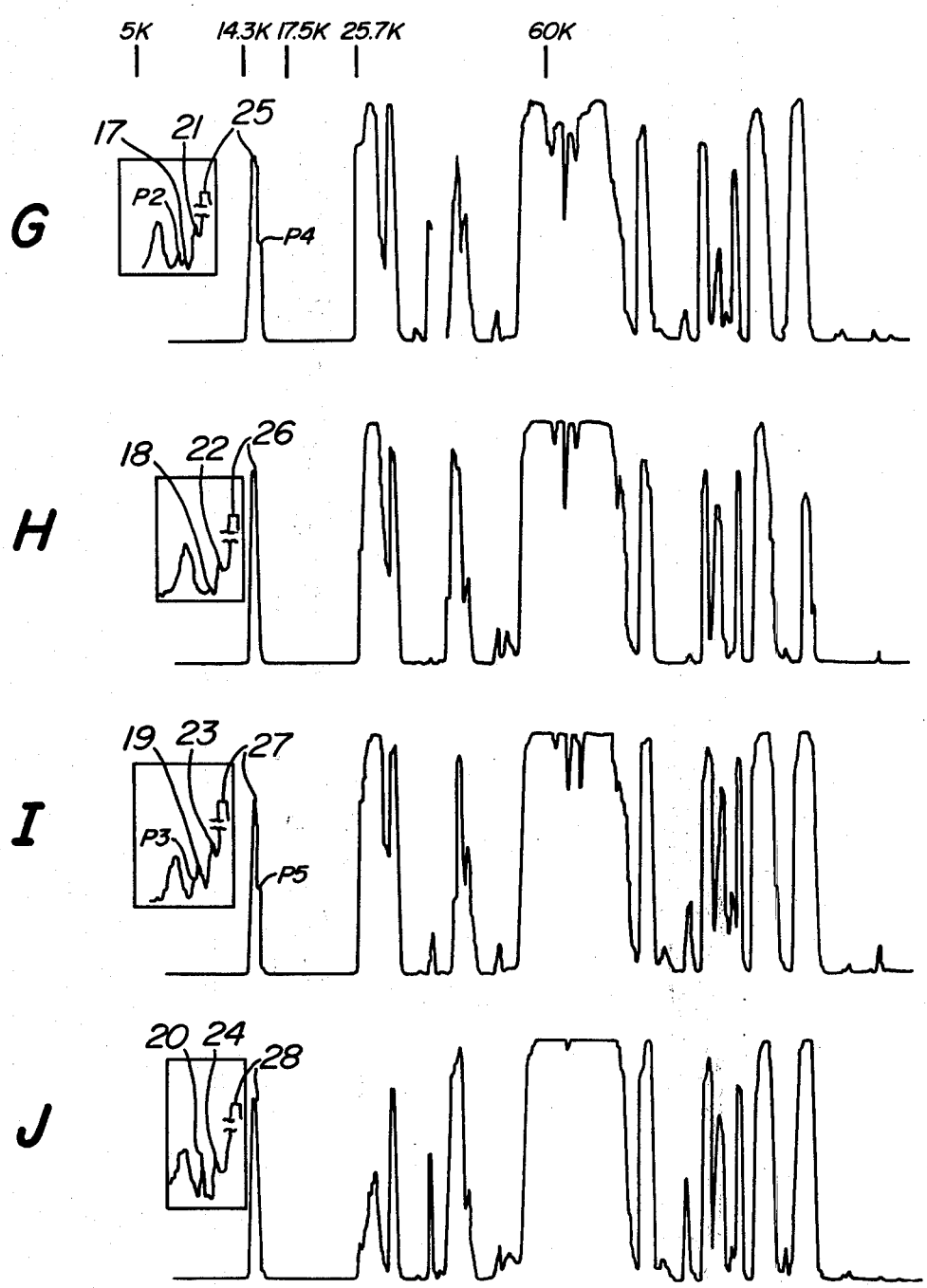
FIG. 8 is a scan of the photograph of FIG. 6 using a soft laser scanning densitometer in a high resolution mode.

Male Sprague-Dawley rats were used and 40 days after being surgically treated as in Example 3, plasma samples were taken, diluted 1:10 with deionized water and the diluted plasma mixed with an equal volume of sample buffer. The blood plasma samples were prepared as described in Example 1. The electrophoretic conditions and compositions were also the same as those in Example 1, including the use of the same five marker proteins. The proteins in aliquots of about 40 μl of sample solutions of blood plasma of the rats were resolved by discontinuous SDS polyacrylamide gel electrophoresis producing gels which were photographed and are reproduced herein as FIGS. 6 and 7. A scan of FIG. 6 using a soft laser scanning densitometer is reproduced in FIG. 8. Like letters and numerals indicate like elements throughout FIGS. 6, 7 and 8. FIG. 7 is an enlargement of the relevant areas of interest of FIG. 6 and will be referred to primarily in this description because of space limitations for labeling the elements in FIG. 6.

With reference to FIG. 7, gel G shows the resolution of proteins in blood plasma of a first ERH rat 40 days after surgical treatment. This rat had a blood pressure of 250/156 mm Hg.

Gel H shows the resolution of proteins in blood plasma of the same rat as in gel G after the surgical removal of the ischemic left kidney resulted in the normalization of blood pressure to a value of 144/100 mm Hg. Thus, gels G and H are of the same rat when it was hypertensive and when it was normotensive, respectively.

Gel I shows the resolution of the proteins in the blood plasma of a second EHR rat 40 days after the surgical treatment. Its blood pressure was 256/172 mm Hg.

Gel J shows the resolution of proteins in the blood plasma of a sham-operated normotensive rat having a blood pressure of 134/96 mm Hg 40 days after the operation. The molecular weights of indicator proteins were also calculated to aid in the determination of the MWr of the proteins associated with hypertension represented by the additional protein bands in the region below 25.7 K in gels G and I of the ERH rats.

Comparing gels G, H, I and J as shown in FIG. 7, two additional protein bands can be detected and identified in gels G and I. Thus, gel G has an additional protein band labeled P2 which corresponds to a protein band P3 in gel I. Protein band P4 in gel G corresponds to protein band P5 in gel I. Further reference may be had to the scan of FIG. 8 (where the peaks are numbered to correspond with the bands of the gels of FIG. 6) and particularly to the higher resolution portions in the boxes adjacent to the main scans. The determination of the relative molecular weights of these proteins associated with hypertension (P2, P3, P4 and P5) is more difficult because of the unusual, but characteristic behavior of these proteins associated with hypertension as will be set forth more fully hereinafter with respect to Example 7.

Bands P2 and P3 are believed to represent the same first protein associated with hypertension with a calculated MWr of about 10,900. Bands P4 and P5 are believed to represent the same second protein associated with hypertension with a MWr of about 14,500. Protein bands 17, 18, 19 and 20 represent the same first indicator protein having a molecular weight of 11,500 daltons. Protein bands 21, 22, 23 and 24 represent the same second indicator protein having a molecular weight of 12,600 daltons. Protein bands 25, 26, 27 and 28 represent the same third indicator protein having a molecular weight of 14,200 daltons.

Based upon molecular weight determinations, the protein or proteins represented by bands P2 and P4 in gel G and by bands P3 and P5 in gel I are not renin, renin-substrate or angiotensin.

This Example is important because it demonstrates that there is very little doubt that protein bands P2 and P4 (and the similar if not identical protein bands P3 and P5, respectively) represent proteins associated with hypertension. This is because the same animal was tested when it was hypertensive and when it was normotensive. When it was hypertensive, its blood plasma included the protein or proteins represented by bands P2 and P4 in gel G. When it was normotensive, bands P2 and P4 were absent in gel H. Thus, almost all other causes for the existence of bands P2 and P4 have been eliminated by testing the same animal.

Based on the unusual migration behavior of these proteins associated with hypertension as explained with regard to Example 7, protein bands P2 and P4 on gel G and protein bands P3 and P5 on gel I may represent the same, single protein associated with hypertension. Alternately, bands P2 and P4 may represent related but separate proteins associated with hypertension. Bands P2 and P4 may represent separate, unrelated proteins, both of which are associated with hypertension. The inventors are uncertain which of these theories is or are correct. The fact is, however, that protein bands P2, P3, P4 and P5 exist in hypertensive rats, but not in normotensive rats.

It appears that the protein represented by band U2 in FIG. 5 is substantially similar to the protein represented by protein band U1 illustrated in FIG. 4. The protein represented by protein bands P3 and P5 of FIGS. 6 through 8 (the same protein may also be represented by bands P2 and P4 of FIGS. 6 through 8 as discussed hereinbefore) may be related to the protein represented by protein band P1 of FIGS. 1 through 3.

Thus, in laboratory rats, it appears that the existence of proteins associated with hypertension in urine and blood plasma indicates a rat is hypertensive, but may not indicate whether the hypertension is genetic hypertension or renal hypertension. This conclusion is not absolute, however. Nevertheless, at least in body fluids of laboratory rats, it is apparent that a protein in a hypertensive rat which is not present in a normotensive rat where the protein has a MWr of about 10,000 daltons to about 17,000 daltons and, more particularly, from about 10,500 daltons to about 16,000 daltons, is a protein which is associated with hypertension.

EXAMPLE 5

This Example is representative of experiments conducted using blood plasma from human patients with essential and secondary hypertension compared to blood plasma from normotensive human subjects.

Blood samples were obtained from hypertensive patients attending an out-patient clinic and from normotensive subjects within a similar age range. Two patients, for this Example, had secondary hypertension (one with renal parenchymal disease and one with renovascular disease) but neither had a family history of essential hypertension. The remaining hypertensive patients for this example all had essential hypertension, secondary hypertension being excluded by the history, clinical examination, urinalysis, serum electrolytes, urea nitrogen and serum creatinine. Rapid sequence pyelography and renal arteriography were preformed, when appropriate, to diagnose renovascular disease.

Venous blood was withdrawn into Vacutainer receptacles containing EDTA and chilled in ice immediately. Plasma and cellular components were separated by centrifugation at 4° C. The plasma was stored at −80°

C. Samples for electrophoresis were prepared as set forth in Example 1. Aliquots of about 40 μl of the samples were then subjected to discontinuous SDS polyacrylamide gel electrophoresis under the conditions and using the compositions set forth in Example 1, including the simultaneous electrophoresis of the same marker proteins. The gels were stained with 0.1% Coomassie Brilliant Blue R 250, and 50% methanol and 10% acetic acid, and destained using 10% methanol and 10% acetic acid.

Figure 9:
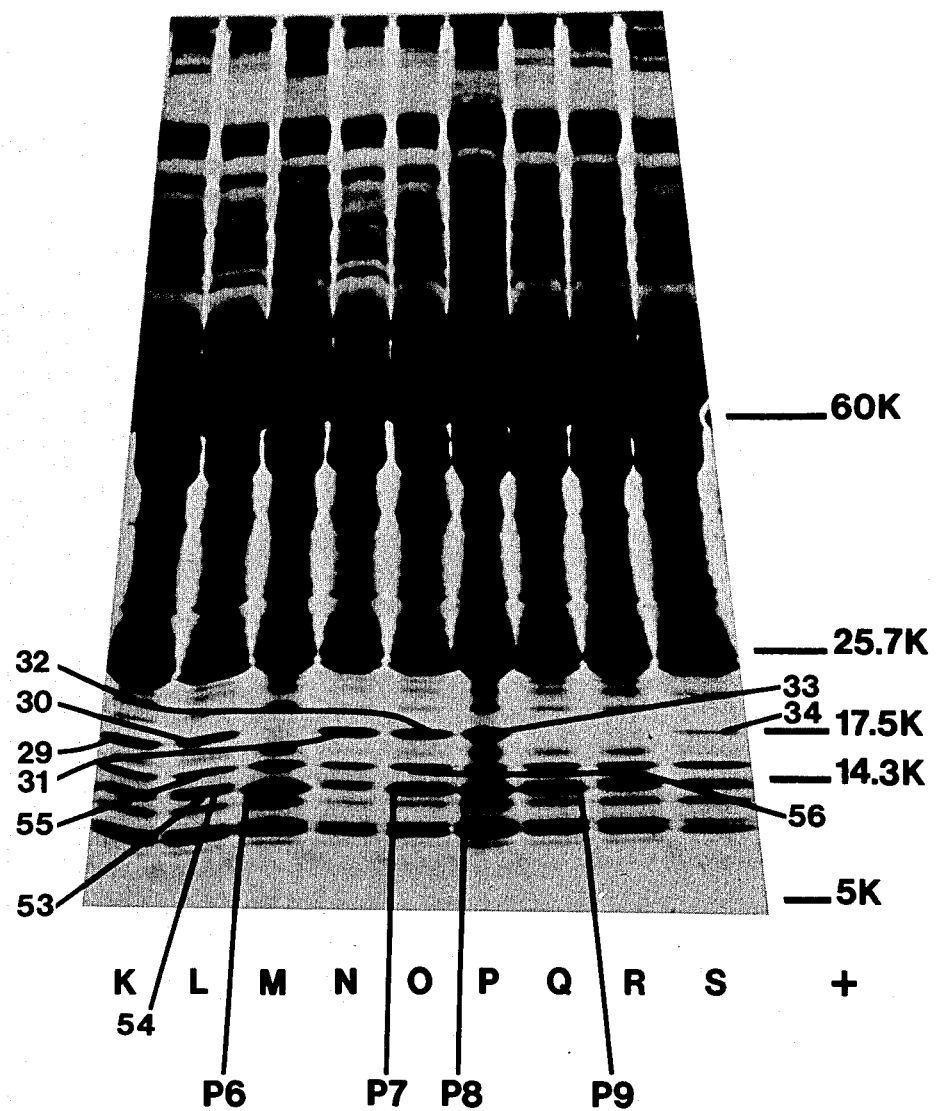
FIG. 9 is a photograph of a SDS polyacrylamide gel comparing protein bands representative of proteins in blood plasma from humans with essential hypertension with protein bands representative of proteins present in blood plasma from humans who are normotensive and from humans with secondary hypertension.

The results of the electrophoretic resolution of the proteins in the blood plasma samples of nine subjects are illustrated in FIG. 9. For ease of understanding, the relevant information is contained in the following table:

TABLE 1

| Subject | Condition | Protein Band Assoc. With Hypertension |
|---|---|---|
| K | RPD(1) | No |
| L | NT(2) | No |
| M | EH(3) | P6 |
| N | NT | No |
| O | EH | P7 |
| P | EH | P8 |
| Q | EH | P9 |
| R | NT | No |
| S | RVD(4) | No |

(1)Renal parenchymal disease and secondary hypertension with no family history of essential hypertension
(2)Normotensive
(3)Essential Hypertension
(4)Renovascular disease and secondary hypertension with no family history of essential hypertension It can be seen by examining the gels of FIG. 9 and the data summarized in Table 1 that the blood plasma of persons having essential hypertension contains an additional protein band representative of a protein having a relative molecular weight of about 14,000. Thus, the gels of subjects M, O, P and Q, all with essential hypertension, have protein bands identified as P6, P7, P8 and P9, respectively. These protein bands are representative of the same protein associated with essential hypertension. Thus, by detecting and identifying the presence of these bands, it is possible to differentiate persons having essential hypertension (M, O, P and Q) from normotensive subjects (L, N and R) and also from persons having secondary hypertension, such as hypertension associated with renal parenchymal disease or renovascular disease (K and S, respectively).

The protein represented by protein bands P6 through P9 has been concluded to be a protein associated with human essential hypertension because it is absent in subjects who do not have a family history of essential hypertension. The presence of protein bands P6 through P9 does not appear to be correlated with age, sex or race. In hypertensive patients, such as subjects K and S whose blood plasma does not contain this protein, the cause of hypertension is non-genetic or non-familial (hence, nonessential), and is due to a variety of secondary causes involving the kidney, kidney artery, adrenal gland or the like.

Protein bands P6 through P9 appear as widened dark areas adjacent to two very closely spaced protein bands, both of which are present in all of the subjects tested. This is because the lower band is representative of two proteins, one of which is associated with essential hypertension. Thus, in gels M, O, P and Q there are actually three proteins represented by the bands in the region of about 14.3 K. The protein associated with hypertension which is represented by each of bands P6 through P9 is not resolved because of a unique but characteristic migration behavior which is displayed during electrophoresis on gels containing horizontal gradients of concentration of polyacrylamide as will be pointed out hereinafter with respect to Example 7. Nevertheless, it is believed that one of ordinary skill in the art would have no trouble discerning the existence of proteins represented by protein bands P6 through P9 once alerted to look for these.

The protein represented by protein bands P6 through P9 is not renin, renin-substrate or angiotensin based upon its relative molecular weight. While its pathophysiologic function is unknown at this time, the protein represented by bands P6 through P9 is important as a marker protein for differentiating essential hypertension from normotension generally, and essential hypertension from secondary hypertension more specifically.

There are some additional differences between the gels of FIG. 9. The differences include the presence of protein bands representative of a protein having a MWr of about 17,500. Band 29 is present in gel K, band 30 is present in gel L, band 31 is present in gel N, band 32 is present in gel O, band 33 is present in gel P and band 34 is present in gel S. The protein represented by bands 29 through 34 does not correlate with sex, race, age or blood pressure. Accordingly, it is merely an inconsistent variation and should not be mistaken for bands P6 through P9 representative of the protein associated with hypertension.

Although the gels of two other subjects tested do not comprise a part of FIG. 9, they are worthy of discussion. Two patients with atherosclerotic renal artery stenosis (resulting in secondary hypertension) superimposed on long-standing essential hypertension were tested. Blood plasma samples from these two patients were subjected to discontinuous SDS polyacrylamide gel electrophoresis as set forth in this Example. The gels of these two patients contained protein bands corresponding to bands P6 through P9. Thus, even when there is evidence of secondary hypertension, so long as a portion of the hypertension appears to be from unknown or genetic factors (that is, essential hypertension), a protein band representative of a protein associated with essential hypertension will exist.

EXAMPLE 6

This Example compares the protein content of blood plasma from human patients with essential and secondary hypertension and from normotensive human subjects using a uniform concentration of resolving gel in a discontinuous SDS polyacrylamide gel electrophoretic analysis.

As in Example 5, blood plasma samples were obtained from patients with essential hypertension and secondary hypertension, as well as from normotensive volunteers within the same age range. One normotensive subject (T) was a 30 year old woman with a strong family history of essential hypertension.

Aliquots of about 40 μl of the samples were subjected to discontinuous SDS polyacrylamide gel eletrophoresis in a vertical orientation in which the resolving gel had a uniform concentration of 13% acrylamide. Other than this difference, the remaining electrophoresis compositions and conditions were the same as those in Example 5.

Figure 10:
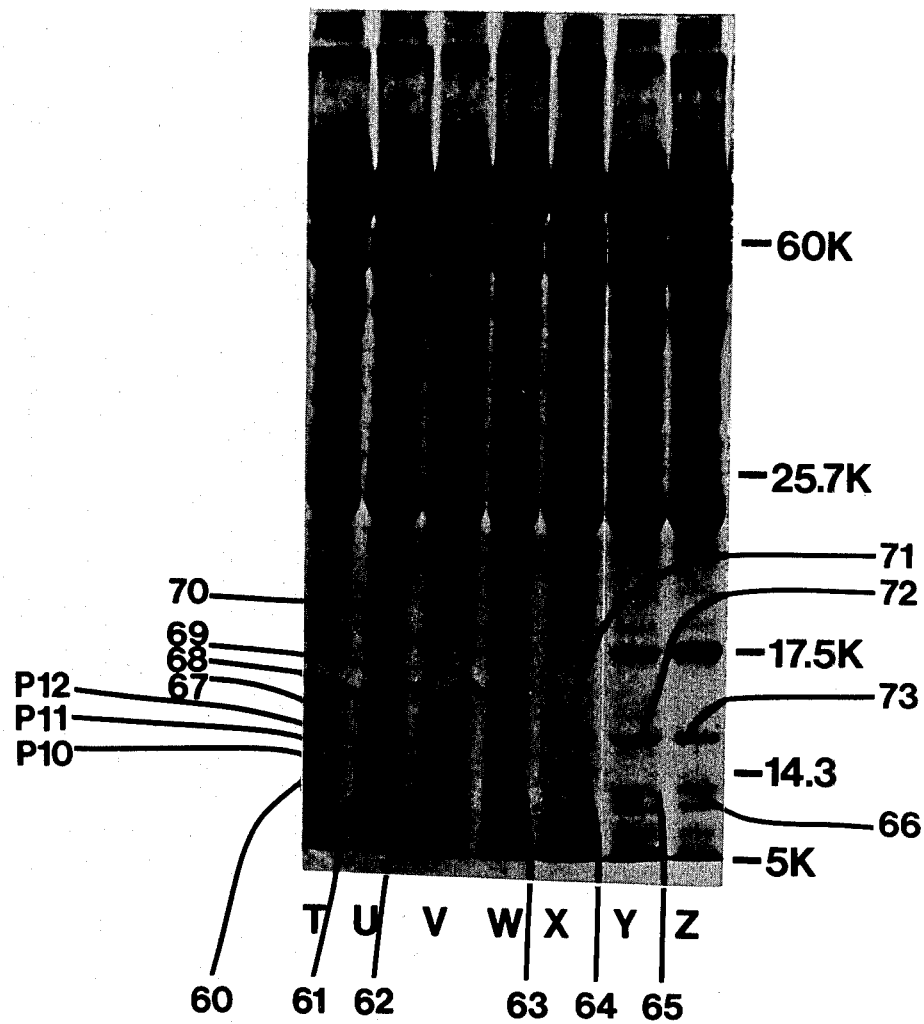
FIG. 10 is a photograph of a SDS polyacrylamide gel having a uniform concentration of polyacrylamide comparing protein bands representative of proteins present in blood plasma from humans with essential hypertension with the protein bands representative of proteins present in blood plasma from normotensive humans and from humans with secondary hypertension.

Further data concerning the subjects and the results of the electrophoretic analysis are summarized in Table 2 and illustrated in FIG. 10.

TABLE 2*

| Subject | Condition | Protein Band Assoc. With Hypertension |
|---|---|---|
| T | NT** | P10 |
| U | EH | P11 |
| V | EH | P12 |
| W | NT | No |
| X | RPD | No |
| Y | RVD | No |
| Z | NT | No |

*The abbreviations in this Table are the same as those in Table 1.
**Family history of essential hypertension.

The results of this Example correlate with the results of Example 5. Thus, subjects U and V, both with essential hypertension, have a protein band representative of a protein associated with hypertension. Band P11 is found in the gel of patient U and band P12 is found in the gel of patient V. Corresponding bands are not found in the gels of any other subjects (except in the gel of subject T to be discussed hereinafter), whether they have secondary hypertension (X and Y) or are normotensive (W and Z). Accordingly, it is believed that the protein represented by bands P11 and P12 is a protein associated with essential hypertension.

An inspection of FIG. 10 reveals the presence of an additional protein band P10 in the gel of subject T, the normotensive young woman with a family history of essential hypertension. Band P10 is in the same region of relative molecular weight as protein bands P11 and P12 which represent a protein associated with the hypertension. The presence of band P10 in the gel of subject T is the only discernible difference in the gel of subject T compared to the gels of the subjects with secondary hypertension (X and Y) and compared to the normotensive subjects without a family history of essential hypertension (W and Z). Accordingly, because of the presence of band P10 in the gel of subject T, it is believed that band P10 is representative of a protein associated with essential hypertension, and may be a link to the genetic or familial cause of essential hypertension. Further, based on the existence and location of band P10 in the gel of subject T, it is believed that band P10 represents the same protein associated with essential hypertension as represented by bands P11 and P12 in the gels of subjects U and V, respectively.

Thus, it is believed that the data supports the conclusion that the detection and identification of this protein may be used as a marker protein for determining the predisposition of a person to essential hypertension. With this information, a normotensive person having this protein can be carefully monitored and/or take preventive actions with respect to the development of essential hypertension.

Protein bands 60 through 66 represent the same first indicator protein having a molecular weight of 14,200 daltons. Protein bands 67 through 73 represent the same second indicator protein having a molecular weight of 15,900 daltons. Based on the molecular weight of the indicator proteins and the marker proteins, the protein represented by bands P10, P11 and P12 has a calculated MWr of 14,700. The protein represented by bands P10 through P12 displays the same relationship to essential hypertension as the protein represented by protein bands P6 through P9. In light of the unusual migratory behavior of the protein associated with hypertension (see Example 7), it is believed that these two proteins are identical. Therefore, the conclusions reached with respect to the protein represented by bands P6 through P9 and bands P10 through P12 apply interchangeably.

EXAMPLE 7

Figure 11:
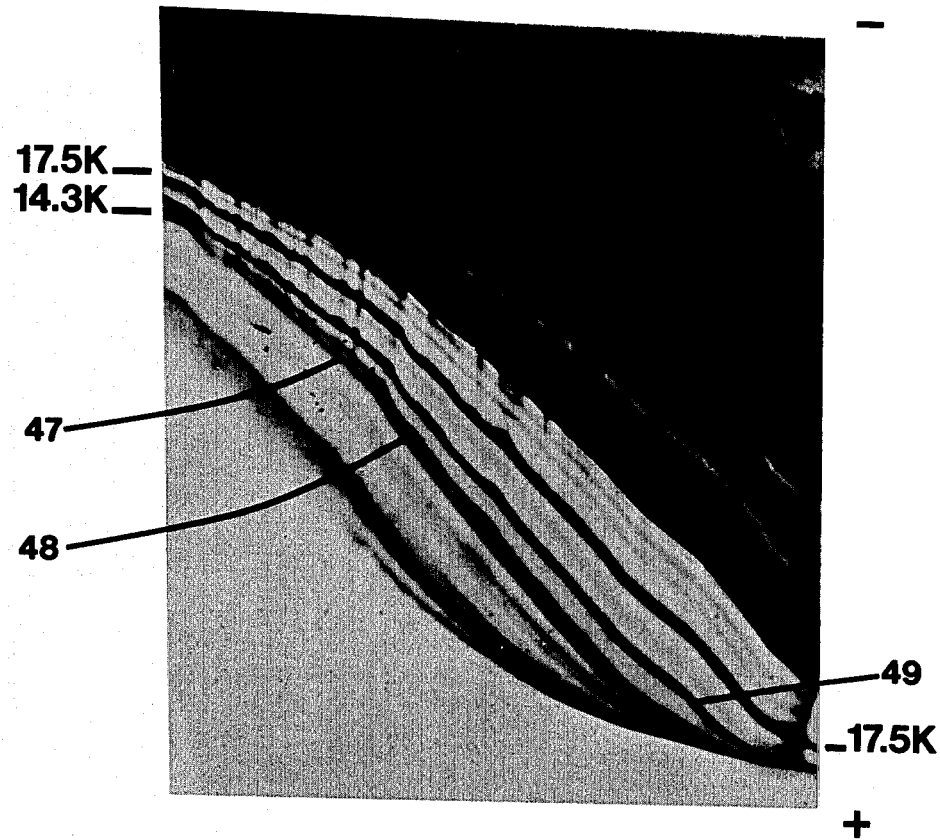
FIG. 11 is a photograph of a SDS polyacrylamide gel using a horizontal polyacrylamide gel concentration gradient showing protein bands representative of the migration of proteins present in blood plasma of a normotensive human.
Figure 12:
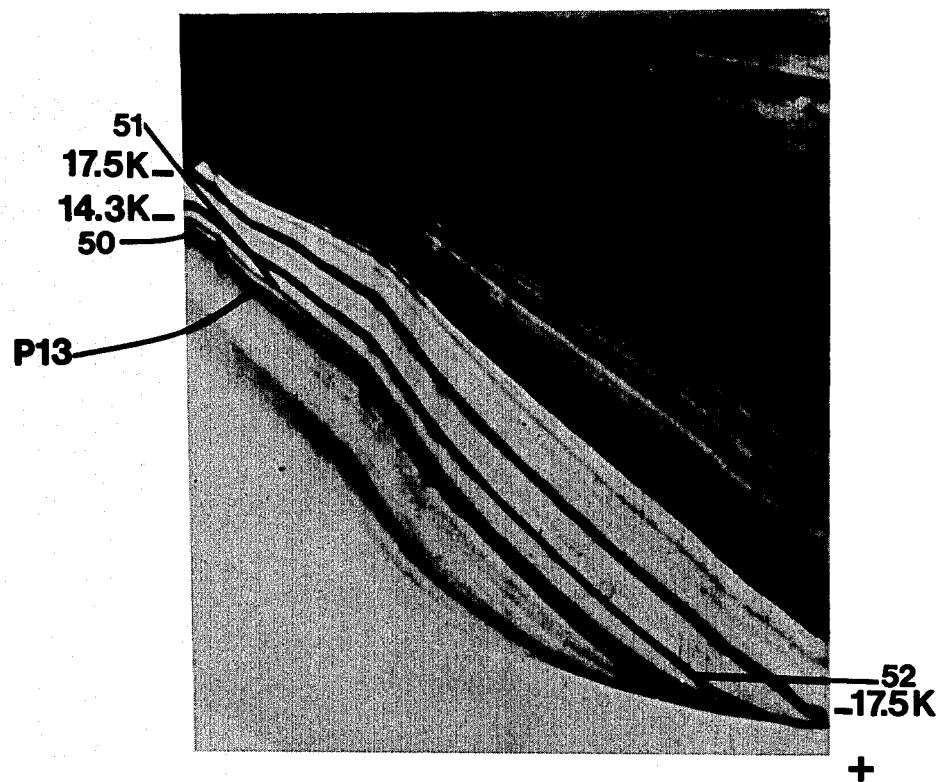
FIG. 12 is a photograph of a SDS polyacrylamide gel using a horizontal polyacrylamide gel concentration gradient showing protein bands representative of the migration of proteins present in blood plasma from a human with essential hypertension.

This Example is representative of experiments which demonstrate the unusual migrating characteristics of the proteins associated with hypertension in the urine and blood plasma of rats and humans as referred to hereinbefore with respect to SDS polyacrylamide gel electrophoresis on gels containing horizontal gradients of concentration of acrylamide. FIGS. 11 and 12 relate to this Example.

The equipment, resolving gel composition, spacer gel composition and buffer electrode composition are the same as in Example 5. Horizontal gradient gels were prepared. A horizontal gradient gel is a gel in which the acrylamide concentration gradient varies from side to side, rather from top to bottom. In a vertical gradient gel, the high concentration of acrylamide is on the bottom and the low concentration of acrylamide is on the top. In the horizontal gradient gels illustrated in FIGS. 11 and 12, the high concentration of acrylamide is on the left and the low concentration of acrylamide is on the right. Thus, the gel plates used in producing the gels of FIGS. 11 and 12 were rotated 90° clockwise before being subjected to electrophoresis when compared to FIGS. 1 and 2, for example. It is only necessary to make sure that the spacer strip is transferred to the open vertical side of the gel plate assembly and sealed before the gel plates are rotated.

The sample solution was prepared as follows. Blood plasma was obtained and treated as in Example 5. 100 μl of the plasma was diluted with 900 μl of deionized water. The diluted plasma was mixed with an equal volume of sample buffer prepared as in Example 1 to form a sample solution. The sample solution (about 2 ml) was electrophoresed as described above in this Example.

FIG. 11 is a photograph of a horizontal gradient gel showing the resolution of proteins in the blood plasma of subject L whose vertical concentration gradient gel is reproduced in FIG. 9. Subject L was a normotensive subject and the gel of FIG. 11 illustrates the usual migration behavior. Band 47 of FIG. 11 corresponds to lower band 53 of the doublet band around the 14.3 K marker of FIG. 9. Band 48 of FIG. 11 corresponds to the upper band 54 of the doublet band in FIG. 9 around the 14.3 K marker. Band 49 of FIG. 11 corresponds to the next higher band 55 on FIG. 9 between the marker proteins at 14.3 K and 17.5 K. On SDS polyacrylamide gels, the $R_f$ (the distance of migration of a protein relative to the ion front) is inversely related to the polyacrylamide concentration at all concentrations of the polyacrylamide in the gel. The $R_f$ is inversely related to the log MW (logarithm of the molecular weight) of the protein. For any given concentration of polyacrylamide, there is a range of molecular weights which displays a linear inverse relationship between $R_f$ and log MW so that the molecular weight of the protein can be determined based upon the $R_f$. Proteins with molecular weights above and below that range deviate from the linear relationship so that the accurate molecular weight of these proteins cannot be determined based upon the particular polyacrylamide gel concentrations involved, and other polyacrylamide gel concentrations must be used for which a linear relationship exists. Usually, as illustrated in FIG. 11, where proteins display a linear relationship between $R_f$ and log MW, the ratio of the $R_f$'s of any two proteins will remain constant (subject to experimental variability) at all concentrations of polyacrylamide.

FIG. 11 illustrates the usual, expected migratory behavior pattern of proteins throughout the gel. It can be seen that each of the bands 47, 48 and 49 is separated from the other by a space. The slopes of bands 47, 48 and 49 are such that the bands do not approach or cross over an adjacent band or adjacent bands representative of a protein or proteins of higher relative molecular weight.

The migratory behavior of proteins associated with hypertension in a horizontal concentration gradient gel is different from the behavior of other proteins as just described. In the case of proteins associated with hypertension comprising the subject of this invention, the ratio of the $R_f$ of the protein associated with hypertension and the $R_f$ of another protein, such as a marker protein, does not remain constant at all concentrations of polyacrylamide within the range where there should be a linear relationship between $R_f$ and log MW of the protein associated with hypertension. Rather, this ratio varies as the concentration of the polyacrylamide varies. Therefore, the log MW of the protein associated with hypertension is not a linear function of its $R_f$. This is an unusual characteristic specific to proteins associated with hypertension within the range of about 10,000 daltons to about 17,000 daltons. The detection of this previously undetected and unidentified specific characteristic has been made possible by the present invention.

This unusual characteristic is illustrated in FIG. 12 which is a photograph of a horizontal gradient gel showing the resolution of proteins in blood plasma of subject 0 in Example 5. Thus, FIG. 12 is a horizontal gradient gel of the vertical gradient gel for subject 0 in FIG. 9.

Protein band 50 in FIG. 12 corresponds to the lower band around 14.3 K of gel O in FIG. 9 (which corresponds in turn to band 53 in gel L in FIG. 9). Band 51 in FIG. 12 corresponds to the upper band of the doublet in gel O of FIG. 9 around 14.3 K (corresponding, in turn, to upper doublet band 54 of gel L in FIG. 9). Band 52 in FIG. 12 corresponds to protein band 55 in gel O in FIG. 9 between the 14.3 K and 17.5 K marker proteins. As was the case with FIG. 11, bands 50, 51 and 52 (which correspond with bands 47, 48 and 49, respectively, in FIG. 11) show the same general spacing and slope as bands 47, 48 and 49 of FIG. 11. This is as it should be, since the ratio of the $R_f$'s of these proteins remain constant.

The major difference between FIGS. 11 and 12 is the existence of an additional protein band P13 in FIG 12 and the different mobility characteristics exhibited by protein band P13. Protein band P13 in FIG. 12 represents the same protein associated with hypertension that was represented by band P7 in gel O of FIG. 9.

In addition to the existence of band P13 in FIG. 12 as a distinguishing characteristic between FIGS. 11 and 12, the migration behavior of band P13 is unusual. Thus, at the top of FIG. 12, band P13 migrates at a position corresponding to a MWr less than 14.3 K and less than the MWr of bands 50 and 51. The protein represented by band P13 has a calculated MWr at the top of the gel of about 13,000. However, in the middle of the gel, band P13 migrated as if it has a higher molecular weight, identical to bands 50 to 51. Band P13 appears to undergo an "inversion" or a "cross-over" with respect to adjacent bands 50 and 51 and approaches band 52. Toward the bottom of FIG. 12, the protein represented by band P13 migrates as if it has a MWr greater than the MWr of bands 50 and 51. The protein associated with hypertension and represented by band P13 has a calculated MWr of about 15,000 at the bottom of the gel. Thus, unlike the other proteins in the gel which have a constant MWr, the MWr of the protein associated with hypertension appears to change. The reason why this occurs is presently unknown. Nevertheless, the fact that this change in slope does occur is a further identification factor for the protein or proteins associated with hypertension.

It must be emphasized that FIG. 12 only illustrates one example of the unusual migratory behavior of a protein associated with hypertension. Thus, while protein band P13 has a slope which approaches or crosses over an adjacent band or bands representative of a protein of higher relative molecular weight, this is so because of the amount of the sample electrophoresed in FIG. 12. Thus, if, for example, 10 $\mu$l of blood plasma were electrophoresed rather than 100 $\mu$l, the amount actually electrophoresed in FIG. 12, perhaps protein bands 50 and 51 (and maybe even band 52) would not be visible on the gel because the proteins they represent are present in only very minute quantities. In that instance, band P13 would not exhibit a "cross-over" behavior because the reference bands would not be visible. Nevertheless, the existence of band P13 and its migration with respect to the other protein bands which are visible would be an indication of the existence of a protein associated with essential hypertension.

The proceding examples provide to one of ordinary skill in the art the ability to practice the present invention. By use of the techniques described herein, as well as the equivalent techniques mentioned hereinbefore, it is possible to detect and identify in a mammal's body fluid a protein or proteins associated with hypertension having a relative molecular weight of about 10,000 daltons to about 17,000 daltons, and more specifically, about 10,500 daltons to about 16,000 daltons and most specifically, about 13,000 daltons to about 15,000 daltons. The protein or proteins associated with hypertension may also be characterized by the unusual mobility characteristics described in Example 7.

By detecting and identifying the protein associated with hypertension, it is possible to determine whether a mammal has hypertension, which is a determination that is frequently not possible to make based on blood pressure measurements alone. Further, at least where humans are concerned, the detection of at least one protein associated with hypertension is an indication that the person has or at least is predisposed to essential hypertension. If a person has high blood pressure and the protein associated with hypertension forming a part of this invention is absent, it indicates the increase in blood pressure is due to an identifiable cause (secondary hypertension). If a person has high blood pressure and the protein associated with hypertension is present, it indicates that there is at least a genetic predisposition to essential hypertension.

The present invention may be embodied in other specific forms without departing from the spirit or essential attributes thereof and, accordingly, reference should be made to the appended claims, rather than to the foregoing specification, as indicating the scope of the invention.

We claim:

1. A process for diagnosing the presence of essential hypertension or a predisposition to essential hypertension in a human comprising detecting the presence in a body fluid of the human of at least one protein associated with hypertension.

2. A process for diagnosing the presence of essential hypertension or a predisposition to essential hypertension in a human who is being tested comprising analyzing a body fluid of the human who is being tested, comparing the analysis of the body fluid of the human who is being tested with at least one reference control analysis of a corresponding body fluid of a control human and detecting in the body fluid of the human who is being tested at least one protein associated with essential hypertension.

3. A process for diagnosing the presence of hypertension or a predisposition to hypertension in a mammal other than a human comprising detecting the presence in a body fluid of the mammal of at least one protein associated with hypertension.

4. A process for diagnosing the presence of hypertension or a predisposition to hypertension in a mammal other than a human which is being tested comprising analyzing a body fluid of the mammal being tested, comparing the analysis of the body fluid of the mammal being tested with at least one reference control analysis of a corresponding body fluid of a control mammal and detecting in the body fluid of the mammal being tested at least one protein associated with hypertension.

5. A process according to claim 1 wherein the presence of the protein associated with essential hypertension is detected by discontinuous sodium dodecyl sulfate polyacrylamide gel electrophoresis.

6. A process according to any one of claims 1 through 4 wherein the body fluid is urine.

7. A process according to any one of claims 1 through 4 wherein the body fluid is a blood fluid selected from the group consisting of plasma and serum.

8. A process according to claim 5 wherein a gradient of concentrations of polyacrylamide gel is used as a resolving gel.

9. A process according to claim 8 further comprising using a horizontal polyacrylamide gel concentration gradient technique to detect the protein associated with hypertension, wherein the protein associated with hypertension is represented by a protein band in a horizontal gradient gel having an $R_f$ value which does not have a constant ratio when compared to the $R_f$ value of another protein band in the horizontal gradient gel at all concentrations of polyacrylamide within a range where the ratios of the $R_f$ values of other protein bands in the horizontal gradient gel are constant.

10. A process according to claim 8 further comprising using a horizontal polyacrylamide gel concentration gradient technique to detect the protein associated with hypertension whereby a horizontal gradient gel is produced containing protein bands representative of individual proteins, the bands having $R_f$ values such that the ratios of $R_f$ values for any two bands are constant for all concentrations of polyacrylamide in the gel within the range of molecular weight (MW) where there is a linear inverse relationship between $R_f$ and log MW of the protein associated with each band, except that the protein associated with hypertension is characterized by $R_f$ values which do not have constant ratios for all concentrations of polyacrylamide in the gel compared with the $R_f$ values of each other protein band within the range.

11. A process according to claim 8 further comprising using a horizontal polyacrylamide gel concentration gradient technique to detect the protein associated with hypertension, wherein there is in a horizontal gradient gel a protein band representative of the protein associated with hypertension which displays migration of the protein associated with hypertension from a first position corresponding to a first relative molecular weight to a second position corresponding to a second relative molecular weight greater than the first relative molecular weight.

12. A process according to claim 8 further comprising using a horizontal polyarylamide gel concentration gradient technique to detect the protein associated with hypertension, wherein the protein associated with hypertension is represented by a protein band in a horizontal gradient gel which crosses over or approaches at least one adjacent protein band in the horizontal gradient gel.

13. A process according to claim 1 wherein the protein associated with hypertension is characterized by an unusual migration behavior in a horizontal gradient gel produced by discontinuous sodium dodecyl sulfate polyacrylamide gel electrophoresis using a horizontal polyacrylamide gel concentration gradient technique.

14. A process according to claim 13 wherein the unusual migration behavior in the gel is evidenced by a protein band representative of the protein associated with hypertension having an $R_f$ value which does not have a constant ratio when compared to the $R_f$ value of another protein band in the horizontal gradient gel at all concentrations of polyacrylamide within a range where the ratios of the $R_f$ values of other protein bands in the horizontal gradient gel are constant.

15. A process according to any one of claims 1 through 4 wherein the protein associated with hypertension has a relative molecular weight of about 10,000 daltons to about 17,000 daltons.

16. A process according to any one of claims 1 through 4 wherein the protein associated with hypertension has a relative molecular weight of about 13,000 daltons to about 15,000 daltons.

17. A process according to claim 3 wherein the protein associated with hypertension is characterized by an unusual migration behavior in a horizontal gradient gel produced by discontinuous sodium dodecyl sulfate polyacrylamide gel electrophoresis using a horizontal polyacrylamide gel concentration gradient technique.

18. A process according to claim 17 wherein the unusual migration behavior in the gel is evidenced by a protein band representative of the protein associated with hypertension having an $R_f$ value which does not have a constant ratio when compared to the $R_f$ value of another protein band in the horizontal gradient gel at all concentrations of polyacrylamide within a range where the ratios of the $R_f$ values of other protein bands in the horizontal gradient gel are constant.

* * * * *